(12) United States Patent
Gross

(10) Patent No.: US 8,020,426 B2
(45) Date of Patent: Sep. 20, 2011

(54) GAS SORPTION TESTER FOR RAPID SCREENING OF MULTIPLE SAMPLES

(75) Inventor: Karl J. Gross, Fremont, CA (US)

(73) Assignee: Hy-Energy, LLC, Newark, CA (US)

( * ) Notice: Subject to any disclaimer, the term of this patent is extended or adjusted under 35 U.S.C. 154(b) by 447 days.

(21) Appl. No.: 12/200,835

(22) Filed: Aug. 28, 2008

(65) Prior Publication Data

US 2009/0071235 A1 Mar. 19, 2009

Related U.S. Application Data

(60) Provisional application No. 60/973,248, filed on Sep. 18, 2007.

(51) Int. Cl.
| | |
|---|---|
| *G01N 7/00* | (2006.01) |
| *G01N 9/00* | (2006.01) |
| *G01N 19/10* | (2006.01) |
| *G01N 25/00* | (2006.01) |
| *G01N 27/00* | (2006.01) |
| *G01N 29/02* | (2006.01) |
| *G01N 33/497* | (2006.01) |

(52) U.S. Cl. ............... 73/23.2; 73/863.31; 73/863.71
(58) Field of Classification Search ........... 73/23.25, 73/23.34, 25.05, 31.06, 31.05, 23.39, 61.53, 73/61.55; 204/424, 429
See application file for complete search history.

(56) References Cited

U.S. PATENT DOCUMENTS

| | | | |
|---|---|---|---|
| 3,850,040 A | 11/1974 | Orr et al. | |
| 5,279,795 A * | 1/1994 | Hughes et al. | ............... 422/98 |
| 5,345,213 A * | 9/1994 | Semancik et al. | ............. 338/34 |
| 5,637,810 A | 6/1997 | Conner, Jr. | |
| 5,798,271 A * | 8/1998 | Godec et al. | ................ 436/146 |
| 6,006,582 A | 12/1999 | Bhandari et al. | |
| 6,096,557 A * | 8/2000 | Tanaka et al. | ................ 436/100 |
| 6,241,950 B1 * | 6/2001 | Veelenturf et al. | ........... 422/537 |
| 6,510,833 B1 * | 1/2003 | Anthon | .................... 123/198 E |
| 6,650,102 B2 * | 11/2003 | Hajduk et al. | ................ 506/12 |
| 7,281,408 B2 | 10/2007 | Srinivasan et al. | |
| 7,288,760 B2 * | 10/2007 | Weitz | ........................... 250/288 |
| 7,767,151 B2 | 8/2010 | Downs | |
| 2003/0079999 A1 | 5/2003 | Penner et al. | |
| 2004/0134258 A1 | 7/2004 | Wang et al. | |
| 2007/0028668 A1 | 2/2007 | Goto et al. | |
| 2009/0263598 A1 * | 10/2009 | Irwin et al. | ................. 428/34.1 |

OTHER PUBLICATIONS

Office Action in U.S. Appl. No. 12/200,839, mailed May 23, 2011.

* cited by examiner

*Primary Examiner* — Lisa M Caputo
*Assistant Examiner* — Roger Hernandez-Prewitt
(74) *Attorney, Agent, or Firm* — Patterson & Sheridan, LLP

(57) ABSTRACT

An apparatus determines gas sorption properties of a large number of material samples simultaneously. The apparatus includes a switchable manifold of low-volume conduits and an array of sensors, where each low-volume conduit fluidly couples a single sample of gas-sorbing material to a dedicated detector. The switchable manifold is also configured to fluidly couple the samples to a vacuum source or a dosing gas source. Because of the very low internal volume of the conduits, essentially all gas released from a particular sample is accurately detected by the corresponding detector, either through sorption of the released gas, by measuring pressure, or by other means. In this way, a very accurate measurement of the quantity of gas released by the sample is made. In one embodiment, the array of sensors includes hydride-based sensors, which contain a material that forms an optically and/or electrically responsive hydride upon exposure to hydrogen-containing gas.

22 Claims, 7 Drawing Sheets

GAS SORPTION TESTER FOR RAPID SCREENING OF MULTIPLE SAMPLES

CROSS-REFERENCE TO RELATED APPLICATIONS

This application claims the priority benefit of the U.S. Provisional Patent Application titled, "METHODS AND APPARATUS FOR COMBINATORIAL DETERMINATION OF SORPTION PROPERTIES," filed on Sep. 18, 2007 and having Ser. No. 60/973,248. The subject matter of this related application is hereby incorporated herein by reference.

BACKGROUND OF THE INVENTION

1. Field of the Invention

Embodiments of the present invention relate generally to devices for performing measurements on small quantities of gases or liquids, and particularly to an apparatus for performing gas sorption measurements on multiple samples of gas-sorbing materials.

2. Description of the Related Art

Synthesis of materials using combinatorial chemistry has been used effectively to produce new materials having small variations in composition and/or structure numbering in the 10s, 100s or 1000s at a time. Such materials processing methods have led to the discovery of new and improved chemicals, pharmaceuticals, semiconductor materials and devices. However, due to the large numbers of different materials involved, combinatorial methods can only lead to timely material discovery when rapid screening of the physical characteristics of the many types of new materials produced thereby is available.

In the case of gas sorption materials, the gas sorption properties of each new material must be tested, i.e., the absorption, adsorption, desorption, physisorption, and/or chemisorption properties, and such testing for even a single sample is a lengthy and labor-intensive process. Such tests include establishing pressure-composition-temperature (PCT) curves for materials, and performing isothermal kinetics and capacity measurements, thermodynamic measurements (van't Hoff curves) and temperature-programmed desorption (TPD) measurements.

The sorption tests for establishing each PCT curve are time-consuming and require very sensitive instrumentation, such as high-accuracy pressure transducers. In addition, collecting information regarding the kinetic sorption properties and thermodynamic stability of gas-sorbing materials typically requires further time-consuming testing of each sample. Thus, characterizing the sorption properties of a new material is a relatively expensive and lengthy process, especially since current testing techniques do not allow rapid screening or testing across multiple samples. In light of the expanding need for characterizing large numbers of new materials, current techniques simply cannot be used to efficiently or cost effectively analyze the large numbers of different materials to be tested, particularly those developed using combinatorial techniques.

Accordingly, there is a need in the art for an apparatus and technique for the rapid screening of multiple gas-sorbing samples.

SUMMARY OF THE INVENTION

One embodiment of the present invention sets forth an apparatus that can determine the gas sorption properties of a large number of material samples simultaneously. The apparatus includes a switchable manifold configured to fluidly couple an array of sensors and an array of samples to a vacuum source, a dosing gas source, and each other. The array of sensors may include pressure transducers, conventional gas detectors, resistivity sensors, and hydrogen-induced phase-change materials including hydride-based sensors.

One advantage of the disclosed apparatus is that can be used to efficiently determine gas sorption properties of a large number of material samples simultaneously and with high accuracy.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

For clarity, identical reference numbers have been used, where applicable, to designate identical elements that are common between figures. It is contemplated that features of one embodiment may be incorporated in other embodiments without further recitation.

DETAILED DESCRIPTION

Embodiments of the invention contemplate an apparatus that determines gas sorption properties of a large number of material samples simultaneously. The apparatus includes a switchable manifold of low-volume conduits and an array of sensors, where each low-volume conduit fluidly couples a single sample of gas-sorbing material to a dedicated detector. The switchable manifold is also configured to fluidly couple the samples and/or sensors to a vacuum source and a dosing gas source. Because of the very low internal volume of the conduits, essentially all gas released from a particular sample is accurately detected by the corresponding detector, either through sorption of the released gas, by measuring pressure, or by other means. In this way, a very accurate measurement of the quantity of gas released by the sample is made. Alternatively, essentially all of the gas in the very low internal volume of the conduits may be absorbed by the sample, the quantity of gas adsorbed or absorbed being measured by the corresponding detector, either through sorption of the released gas, by measuring pressure, or by other means. In one embodiment, the array of sensors includes hydride-based sensors, which contain a material that forms an optically and/or electrically responsive hydride upon exposure to hydrogen-containing gas.

Figure 1:
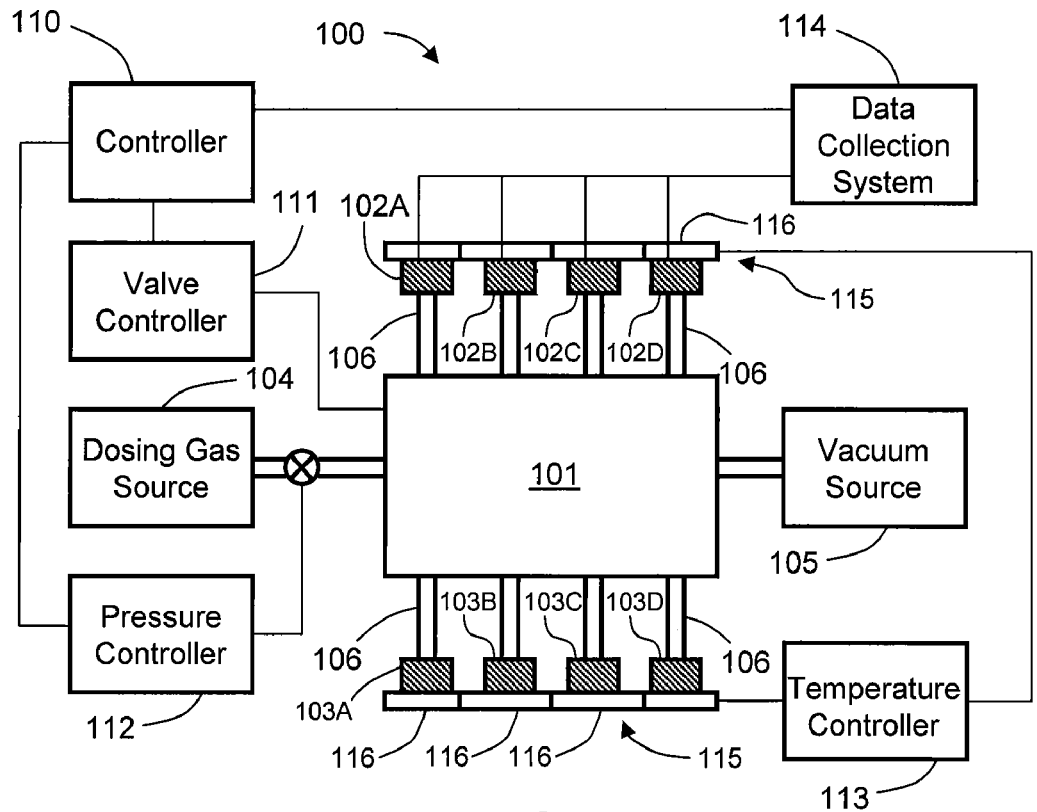
FIG. 1 is a schematic diagram of a gas sorption apparatus configured to perform tests on multiple samples simultaneously, according to an embodiment of the invention.

FIG. 1 is a schematic diagram of a gas sorption apparatus 100 configured to perform tests on multiple samples simultaneously, according to an embodiment of the invention. The principle components of gas sorption apparatus 100 include a switchable manifold 101, an array 102 of sensors 102A-D, a plurality of samples 103A-D, a dosing gas source 104 and a vacuum source 105. For improved performance, gas sorption apparatus 100 may also include a controller 110 coupled to a valve controller 111, a pressure controller 112, a temperature controller 113, a heater assembly 115, and a data collection system 114. Controller 110 is an electronic controller, such as a microprocessor, and is configured to control the operation of gas sorption apparatus 100, e.g., valve operation, pressure control, vacuum control, electronic data collection, temperature control and/or dosing quantity and frequency.

Switchable manifold 101 is configured to fluidly couple samples 103A-D to detectors 102A-D by means of a low volume path. To that end, switchable manifold 101 includes low-volume conduits 106. For improved accuracy of gas sorption tests performed by gas sorption apparatus 100, the internal volume of low-volume conduits 106 is advantageously minimized. In one embodiment, low-volume conduits 106 comprise small-diameter electro-polished stainless steel tubing, having an internal diameter of 2 mm or less. In an alternative embodiment, low-volume conduits 106 may be small-diameter holes formed through the body of switchable manifold 101, e.g., by laser drilling, chemical growth, chemical etching, or other techniques. In such an embodiment, low-volume conduits 106 may have outer diameters as small as 1 micron. Thus, the total free volume between a given sample and corresponding sensor may be 0.1 ml or less.

The material in which low-volume conduits 106 are formed preferably is characterized by low gas-permeability and out-gassing, such as stainless steel, glass, ceramic materials, alumina, Macor™, and other ultra-high vacuum (UHV) compatible materials. In one embodiment, low-volume conduits 106 may be configured to thermally isolate sensors 102A-D from samples 103A-D, so that each sensor may be maintained at a substantially different temperature than its corresponding sample. For example, low-volume conduits 106 may be formed from small-diameter tubing that conduct very little heat. Alternatively, low-volume conduits may be drilled or formed through a solid block of thermally insulative material, e.g., alumina. In this way, the samples and sensors are thermally decoupled, allowing greater flexibility in the type of sorption tests performed by gas sorption apparatus 100.

Switchable manifold 101 also includes one or more very low-displacement valves, such as such as rotating valves and/or sliding valves, for fluidly coupling and decoupling sensors 102A-D from samples 103A-D, respectively as well as for fluidly coupling sensors 102A-D from samples 103A-D from dosing gas source 104 or vacuum source 105. Very low-displacement valves are known in the art, and are well suited for applications in which conduits formed through a solid material need to be sealed. For example, a very low-displacement valve or valves may be incorporated into the body of the Switchable manifold 101 as a system of rotating or sliding plates with fluid coupling holes and grooves between sealing gaskets. In addition, use of very low-displacement valves may substantially reduce error in pressure- and volume-dependent measurements, such as PCT measurements. An example of the mechanical organization and operation of a sliding valve 406 is described below in conjunction with FIG. 4A.

Array 102 includes a plurality of sensors 102A-D, each of which is fluidly coupled to a single low-volume conduit 106. Sensors 102A-D may be individually positioned in fluid contact with low-volume conduits 106, as shown in FIG. 1. Alternatively, sensors 102A-D may be configured as a single assembly or sensor array, as described below in conjunction with FIGS. 5-7. It is contemplated that sensors 102A-D may be selected from a wide variety of possible sensor types, depending on the particular dosing gas used and specific test being performed. Sensors that may be used in array 102 include pressure transducers and conventional gas detectors. In one embodiment, when the dosing gas is a hydrogen-containing gas, array 102 may include hydride-based sensors, which contain a material that forms an optically and/or electrically responsive hydride upon exposure to hydrogen-containing gas. For clarity, gas sorption apparatus 100 is illustrated in FIG. 1 with only four sensors 102A-D, and array 102 is depicted as a linear array. However, embodiments of the invention contemplate array 102 containing a large number of sensors, e.g., 10s or 100s of sensors. Further, the sensors making up array 102 may be arranged in a two-dimensional array, as illustrated below in FIG. 8, the two-dimensional array having a means to fluidly separate each detector one-from-another. The sensors or sensor arrays may be replaceable to allow sensor types to be changed depending on the experimental conditions, or easily replaced when contaminated or not functioning.

As noted above, sensors A-D of array 102 may be pressure transducers, which are high-accuracy pressure measuring device capable of detecting changes in relative or absolute pressure in each of low-volume conduits 106 to the degree necessary for performing gas sorption tests. For example, types of pressure transducers suitable for use in array 102 include a strain-gauge pressure transducer, a piezoelectric pressure transducer, or a capacitance manometer, such as a Model 870B Micro-Baratron® or chip-based micro-pressure-sensors. In one embodiment, each sensor in array 102 may include an array of multiple pressure transducers, each having a different operating pressure range.

When array 102 includes pressure transducers, gas sorption apparatus 100 may be used as a Sievert's device to perform a PCT measurement or a TPD measurement of specific gases as they are absorbed or desorbed from each of samples 103A-D. In this embodiment, each of sensors 102A-D may also include a temperature sensor. In this way, the temperature and pressure of the dosing gas being tested are both known. As noted above, during testing, sensors 102A-D are fluidly coupled to samples 103A-D, respectively, via low-volume conduits 106. Because the internal volume of low-volume conduits 106 is a small and accurately known volume, the pressure changes that occur in the volume between sensors 102A-D and samples 103 due to sorption or desorption of a dosing gas are compounded. Therefore, the mass of dosing gas that flows into or out of each material sample can be very accurately determined.

Array 102 may include conventional gas sensors known in the art, such as flammable gas detectors or other gas sensors. In this embodiment, sensors 102A-D may be used to quantify the amount of dosing gas released from or absorbed by samples 103A-D based on a property change of a reactive material contained in the sensor, such as resistivity change.

Because the resistivity of the reactive material may be function of how much dosing gas is present, the quantity of desorbed dosing gas is easily measured. Alternatively, array 102 may include fuel cell-based sensors, which are designed to produce a voltage upon reaction with a dosing gas, particularly hydrogen-containing gases. In yet another alternative embodiment, array 102 may include thermal conductivity or gas resistivity sensors that measure the density of gas within the low-volume conduits 106. It is noted that the accuracy of measurements based on sensor reaction with the dosing gas may be enhanced by the configuration of gas sorption apparatus 100 since the internal volume of low-volume conduits 106 is a small, known volume. An exemplary embodiment of a sensor using an electrically responsive material is described below in conjunction with FIG. 5.

In one embodiment, array 102 may include hydride-based sensors, which contain a material that forms an optically and/or electrically responsive hydride upon exposure to hydrogen-containing gas. Hydride-forming materials, as defined herein, include any material that changes physical properties on contact with hydrogen, and is not meant to necessarily imply the formation of a stoichiometric hydride compound. Hydride-forming materials that may be used in hydride-based sensors include yttrium (Y), lanthanum (La), magnesium-titanium (Mg—Ti) alloys, magnesium-nickel (Mg—Ni) alloys, and various palladium (Pa) alloys. In fact, most hydrides undergo some optical transformations and/or electrical property changes during formation from a non-hydrided material. Therefore, many other possible hydride-forming materials may also be used to some effect in such sensors. Again, the low internal volume of low-volume conduits 106 is beneficial for improved accuracy of measurements. An exemplary implementation of an optically responsive hydride-based sensor is described below in conjunction with FIGS. 6 and 7.

Yttrium is one example of an optically responsive material that may be used in a hydride-based sensor, according to an embodiment of the invention. Yttrium is highly reflective at visible wavelengths, and forms hydrides ($YH_2$ and $YH_3$) that each have different reflectivities. $YH_2$ is slightly less reflective than yttrium, and $YH_3$ is nearly transparent. Therefore, when hydrogen gas is brought in contact with yttrium, an optical detector will register less light reflected from the surface of the yttrium as more hydrogen is absorbed by the yttrium. A correlation between the quantity of hydrogen gas absorbed and the intensity of light registered by the optical detector can be constructed, so that the reflectance of the sensor indicates the quantity of gas that has been absorbed by the detector and, therefore, released by the sample. Such processes are most advantageous when the detector material is reversible under typical operating conditions, however it is contemplated that one-time-use only detectors may be used. Some materials, such as yttrium, may require an active, gas-transparent coating, such as a palladium cap to prevent oxidation of the yttrium and possibly also act as a catalyst for dissociation of the active gas such as hydrogen.

Each of samples 103A-D includes a material sample prepared for sorption testing. Hence, each material sample is isolated from the ambient environment in an gas-tight fashion and held in a small-volume chamber. Each material sample may be a thin-film material deposited on a substrate, a bulk sample, or any other morphology conducive to sorption testing, such as a bulk sample that has been pulverized. In one embodiment, a filter may be disposed between each sample and the low-volume conduit 106 fluidly coupled thereto, to prevent contamination and fouling of the low-volume conduit 106 by the sample material. As described above regarding sensors 102A-D, each of samples 103A-D may be individually positioned in fluid contact with low-volume conduits 106, as shown in FIG. 1. Alternatively, samples 103A-D may be configured as a single assembly, such as a sample library. Sample libraries, according to embodiments of the invention, are described below in conjunction with FIG. 3.

Valve controller 111 operates pressure controller 112 and the very low-displacement valves contained in switchable manifold 101, thereby establishing the connections between dosing gas source 104, vacuum source 105, samples 103A-D, and sensors 102A-D. Pressure controller 112 controls the pressure of gas introduced into switchable manifold 101 from dosing gas source 104, which is beneficial for certain sorption measurements. The control valve may consist of a manual or software-controlled pressure regulator, a flow control device, or needle valve. Temperature controller 113 controls the individual heaters 116 that make up heater assembly 115, to maintain each of samples 103A-D and sensors 102A-D at a prescribed temperature or temperature history, such as a controlled temperature ramping rate. As shown in FIG. 1, an individual heater 116 may be positioned in proximity to each of samples 103A-D and/or sensors 102A-D. Controlling the sample and detector temperature aids in performing certain sorption measurements. Data collection system 114 is configured to obtain information from each of sensors 102A-D. The information may be obtained, for example, by an electrical connection, an optical connection, or though an optical system that images the sensors.

In operation, gas sorption apparatus 100 is configured to perform one or more sorption tests simultaneously on a plurality of samples. Depending on the type of sensors in array 102, gas sorption apparatus 100 may perform PCT and TPD tests on samples 103A-D and generate kinetic and thermodynamic stability information about the samples. In the course of such testing, switchable manifold 101 fluidly couples samples 103A-D and/or sensors 102A-D, to dosing gas source 104, and to vacuum source 105, as well as to each other. FIGS. 2A-G schematically illustrate various operations performed by gas sorption apparatus 100 in the course of such sorption testing, according to different embodiments of the invention.

Figure 2A:
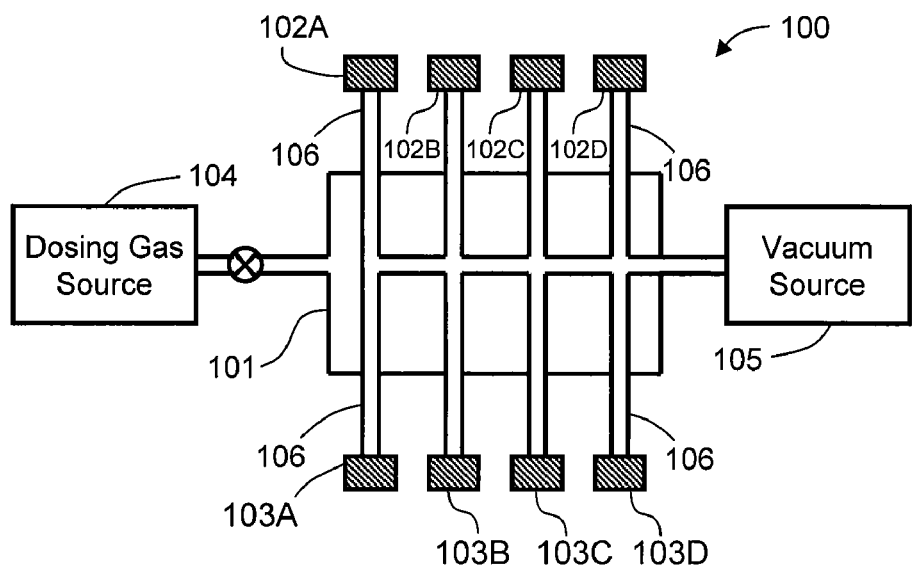
FIGS. 2A-G schematically illustrate different operations performed by a gas sorption apparatus in the course of sorption testing, according to embodiments of the invention.
Figure 2B:
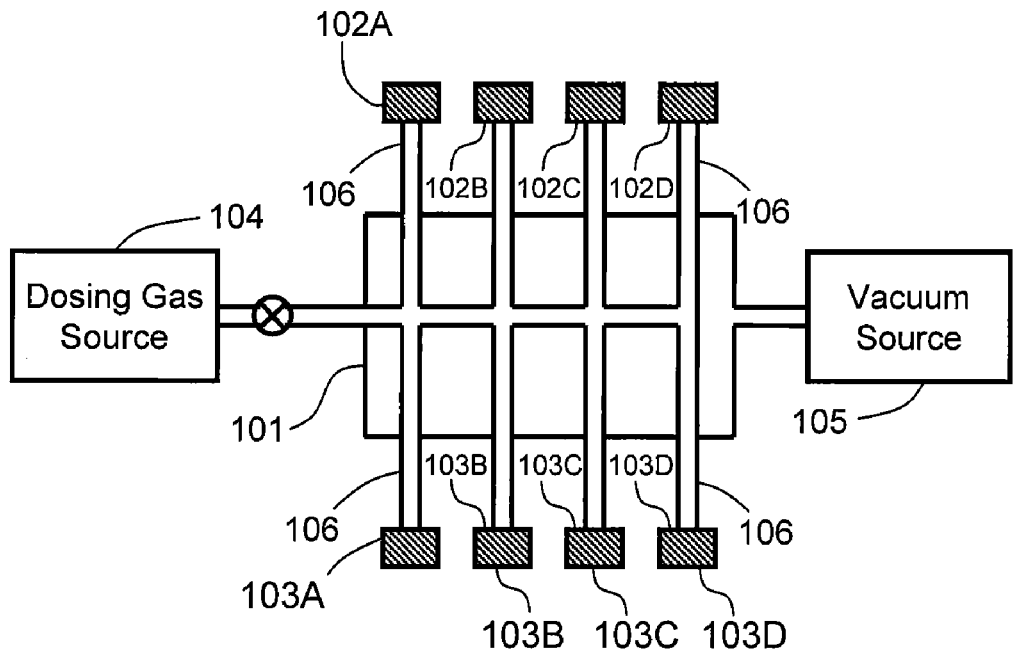
Figure 2C:
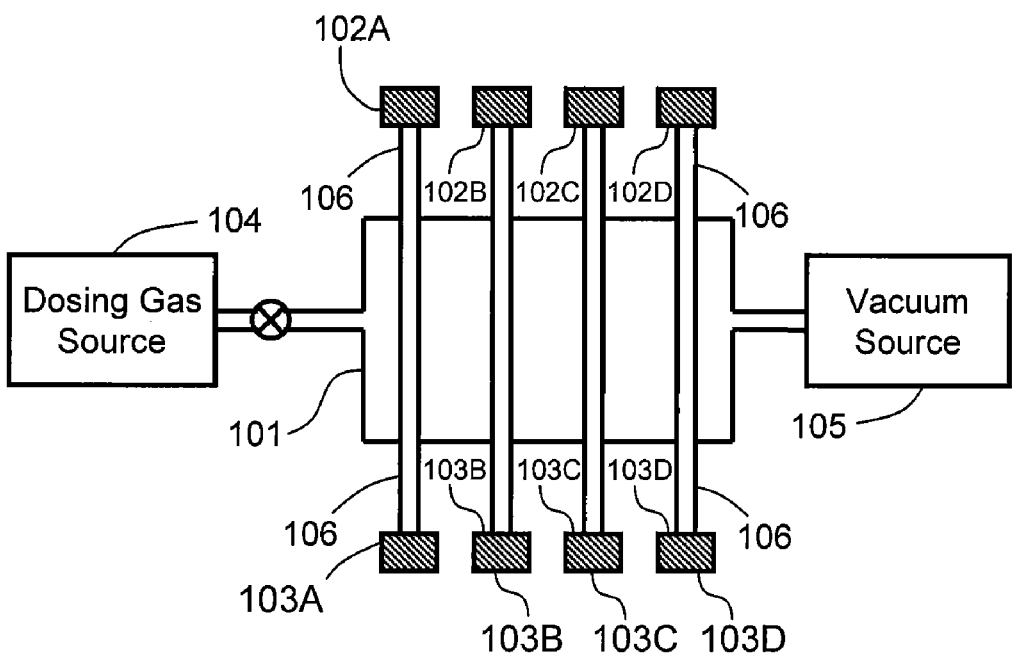
Figure 2D:
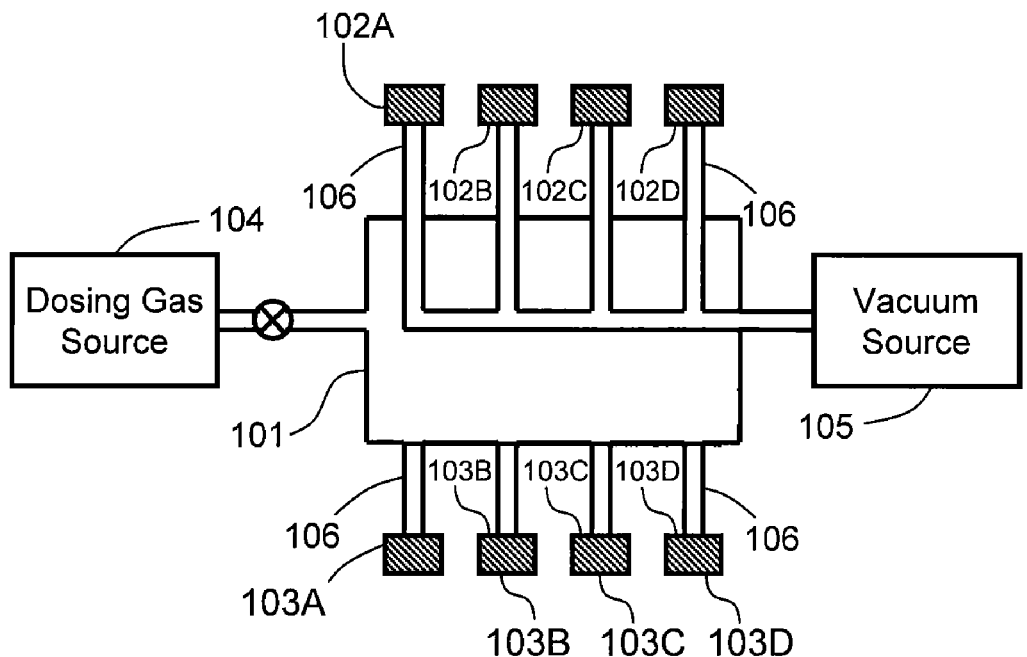
Figure 2E:
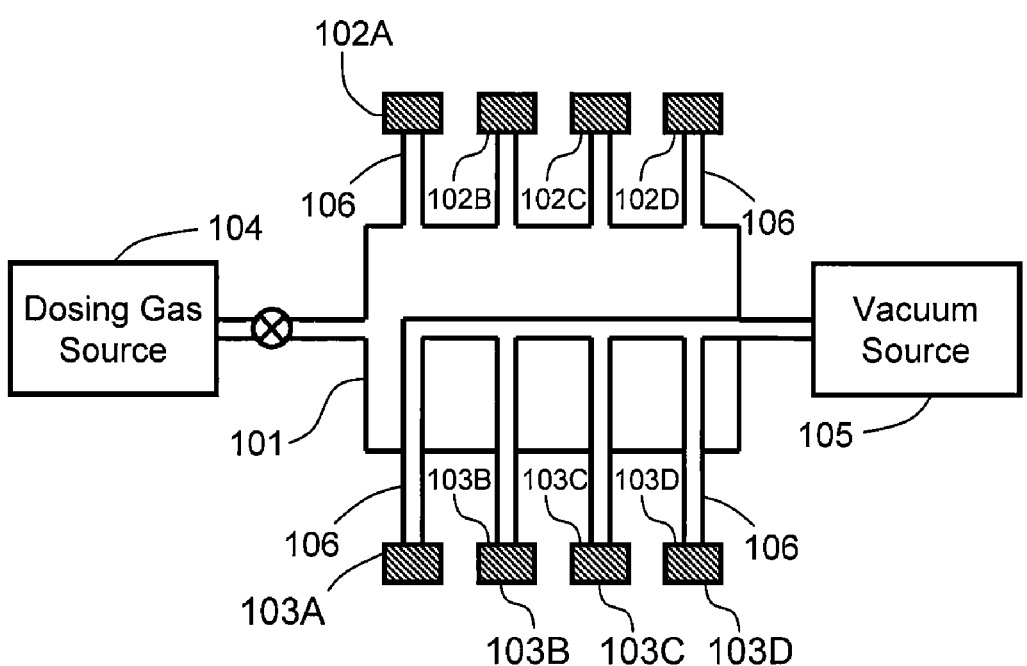
Figure 2F:
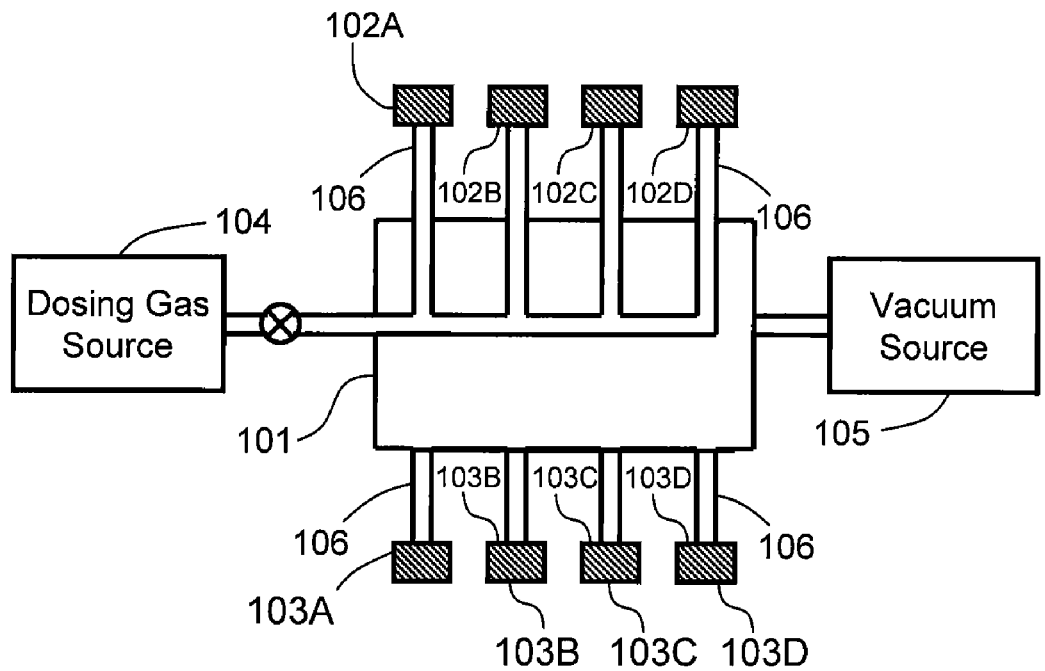
Figure 2G:
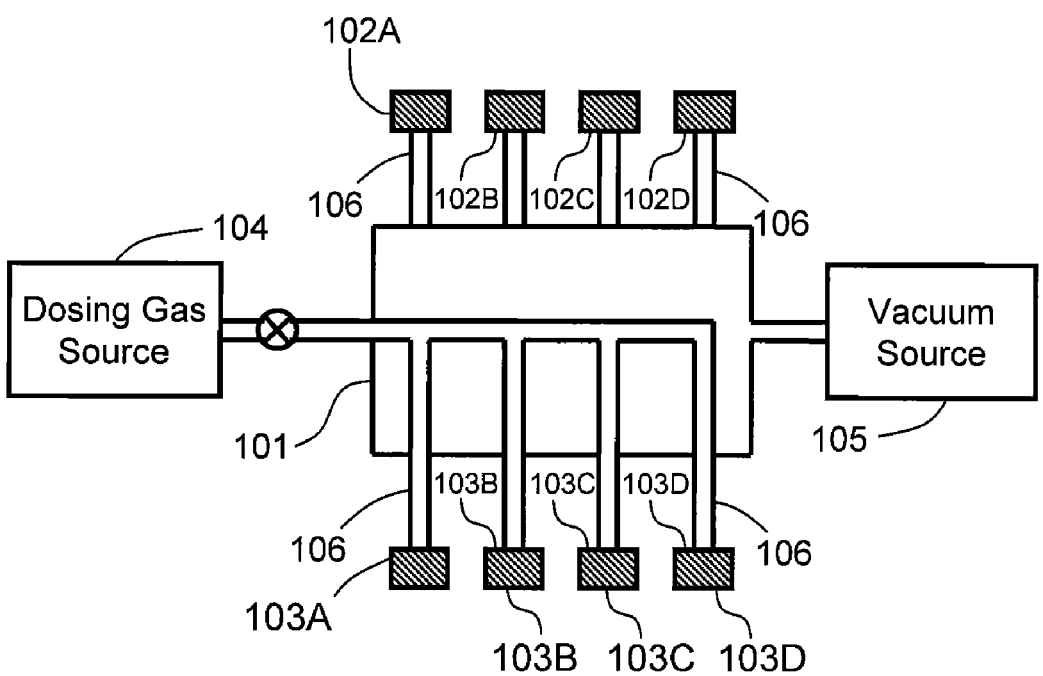

FIG. 2A schematically illustrates gas sorption apparatus 100 with switchable manifold 101 positioned to fluidly couple samples 103A-D and sensors 102A-D to vacuum source 105 for evacuation of any gases contained therein. Evacuation may be performed as part of a preparation process for testing of samples 103A-D. FIG. 2B schematically illustrates gas sorption apparatus 100 with switchable manifold 101 disposed to fluidly couple samples 103A-D to dosing gas source 104 for fully charging samples 103A-D and sensors 102A-D in preparation for desorption PCT dosing measurements. FIG. 2C schematically illustrates gas sorption apparatus 100 with switchable manifold 101 positioned to fluidly couple each of samples 103A-D to a corresponding sensor 102A, 102B, 102C, or 102D. In this configuration, each of sensors 102A-D are in direct "gas contact" to a corresponding sample by means of a fluid path that has very little, if any, free volume, i.e., a low-volume conduit 106. FIG. 2D schematically illustrates gas sorption apparatus 100 with switchable manifold 101 positioned to fluidly couple each of sensors 102A-D to vacuum source 105, to pump-down sensors 102A-D. FIG. 2E schematically illustrates gas sorption apparatus 100 with switchable manifold 101 positioned to fluidly couple each of samples 103A-D to vacuum source 105, to pump-down samples 103A-D. FIG. 2F schematically illustrates gas sorption apparatus 100 with switchable manifold 101 positioned to fluidly couple each of sensors 102A-D to dosing gas source 104, to charge sensors 102A-D with a dosing gas. FIG. 2G schematically illustrates gas sorption apparatus 100 with switchable manifold 101 positioned to fluidly couple each of samples 103A-D to dosing gas source 104, to charge samples 103A-D with a dosing gas.

In FIGS. 2A-G, the fluid coupling and decoupling of sensors 102A-D and samples 103A-D to dosing gas source 104, vacuum source 105, as well as to each other, are shown schematically. One skilled in the art will readily understand how to configure low-volume conduits 106 and sliding and/or rotating valves to allow such fluid coupling to take place, as is described herein. Further, while fluidly coupling samples 103A-D or sensors 102A-D to dosing gas source 104, vacuum source 105, and/or to each other, simultaneously may be advantageous, individually controlling the fluid coupling of each of samples 103A-D and/or sensors 102A-D by switchable manifold 101 also falls within the scope of the present invention. Although more complex, one of skill in the art will readily understand how to configure a system of sliding and/or rotating valves that allows such individual connection of samples 103A-D or sensors 102A-D, as needed.

By way of example, an absorption PCT measurement procedure is described with respect to the different configurations of gas sorption apparatus 100 illustrated in FIGS. 2A-G. First, sensors 102A-D and samples 103A-D are evacuated, as shown in FIG. 2A. Next, samples 103A-D are isolated and dosing gas is introduced to sensors 102A-D, as illustrated in FIG. 2F. Sensors 102A-D are then fluidly coupled to samples 103A-D as illustrated in FIG. 2C, and the change in gas concentration in each of sensors 102A-D and corresponding low-volume conduits 106 is measured as each of samples 103A-D absorb the dosing gas. The quantity of gas change in each of sensors 102A-D and low-volume conduits 106 is used to calculate the quantity of gas absorbed by each of samples 103A-D, and a point on the PCT curve for each sample is plotted. This procedure is then repeated at increasingly higher pressures to generate additional points and thereby construct a full PCT curve for each of samples 103A-D. Desorption PCT curves may be performed in the same manner, except that one would start by fully charging the sample and detectors at the highest pressure by exposing both samples 103A-D and sensors 102A-D to the gas source at highest pressure and then dosing gas out of each sample by decreasing the pressure in the sensor and conduit in steps as above.

It is noted that in principal one would really need each of sensors 102A-D to be pressure sensors rather than concentration sensors to construct true equilibrium PCT curves, since the final equilibrium pressure should be known at each dose and because concentration can be determined in the classic Sieverts method by knowing the volume, gas temperature and pressure change. Due to the difficulty in making an array of highly accurate, separate pressure sensors, it is contemplated that, in one embodiment, gas sorption apparatus 100 may perform such measurements in an easier but less accurate way. To wit, a concentration sensor, such as the metal-hydride optical sensors described below in conjunction with FIGS. 6 and 7, measures only the concentration change with each dose. This concentration change may be plotted versus the applied dosing pressure, which may be taken from a single pressure sensor at the dosing gas supply line. In this way the storage capacity of each of samples 102A-D is quantified and an approximate PCT plot constructed. By taking very regular steps in dosing gas pressure, or at least knowing the difference in source pressure between steps and measuring the concentration change, it is possible to back calculate the equilibrium pressure for each sample to construct the true PCT curve.

Kinetics and TPD measurements can also be performed by gas sorption apparatus 100, by configuring gas sorption apparatus 100 as illustrated in FIGS. 2A-G. Since such measurements are concentration vs. time and concentration vs. temperature, it is not necessary to have individual pressure sensors for each sample for these measurements.

Figure 3:
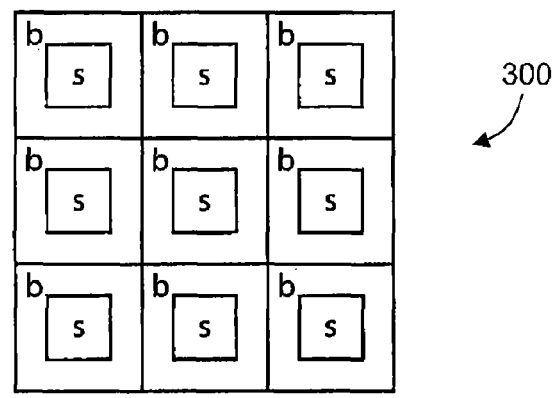
FIG. 3 is a schematic illustration of a sample library, according to an embodiment of the invention.

In one embodiment, samples 103A-D are arranged in a sample library, which is positioned in fluid contact with low-volume conduits 106 prior to sorption testing. FIG. 3 is a schematic illustration of a sample library 300, according to an embodiment of the invention. Sample library includes a plurality of sample areas s, each surrounded by a border b. Sample areas s are discretized regions on the surface of a substrate, such as a glass substrate, metal substrate, or silicon wafer. Each of sample areas s may include a different material composition. The plurality of material compositions contained in sample library 300 may be formed thereon by any known combinatorial techniques or other technically feasible approaches including discrete or continuous deposition techniques. For example, a continuous spectrum of material compositions of continuously varying mixtures may be formed over the substrate of sample library 300 using co-deposition of different materials on the substrate. The sample areas s then discretize the continuously varying mixtures on the substrate, dividing the substrate into small areas of approximately constant composition. In this way, a large number of samples of different compositions can be quickly prepared and simultaneously measured using gas sorption apparatus 100. In one embodiment, one or more sample areas s in sample library 300 contain material compositions of known sorption properties, to be used for reference or calibration purposes.

The size of each sample area s may be relatively small, so that a large number of different material compositions, e.g., 10s or 100s, can be contained in a single sample library and tested simultaneously by gas sorption apparatus 100. The minimum area of each sample area s is only limited by the practical limitations of the minimum width of border b and the accuracy desired for a given sorption test. Since smaller sample areas s are capable of absorbing and desorbing less total gas, the accuracy of any sorption test can be adversely affected as the area of each sample area s is reduced and as the thickness of each sample area s is reduced.

The material of border b is selected to form a gas or liquid barrier between the samples, so that each sample area s may be completely isolated from adjacent sample areas during sorption testing. In one embodiment, border b is simply a region of sample library 300 in which no sample material has been deposited. In another embodiment, border b includes an isolation member. The isolation member may be a raised sealing material used to establish a gas-tight seal with low-volume conduits 106. In this embodiment, the surface of switchable manifold 101 may be a smooth, polished surface against which the isolation member is pressed, thereby isolating each sample area s from adjacent sample areas while fluidly coupling each sample area s to a corresponding low-volume conduit 106.

Because the quantities of gas that are sorbed and desorbed from thin-film samples are extremely small, even a small quantity of gas outgassing from the isolation member can adversely affect the accuracy of a sorption test. Consequently, it is contemplated that the isolation member may be formed from a material that is subject to essentially no outgassing or gas permeability over the wide range of temperatures and pressures associated with sorption tests. Many UHV-compatible materials may be used for this purpose and are well-known, such as a O-rings or UHV high-temperature epoxy. In another example, the isolation member may be a grid deposited in border s, the grid being formed from a relatively soft metal, such as nickel or copper. In another embodiment, the isolation member is incorporated into a surface of switchable manifold 101, as described below in conjunction with FIGS. 4A, B.

Figure 4A:
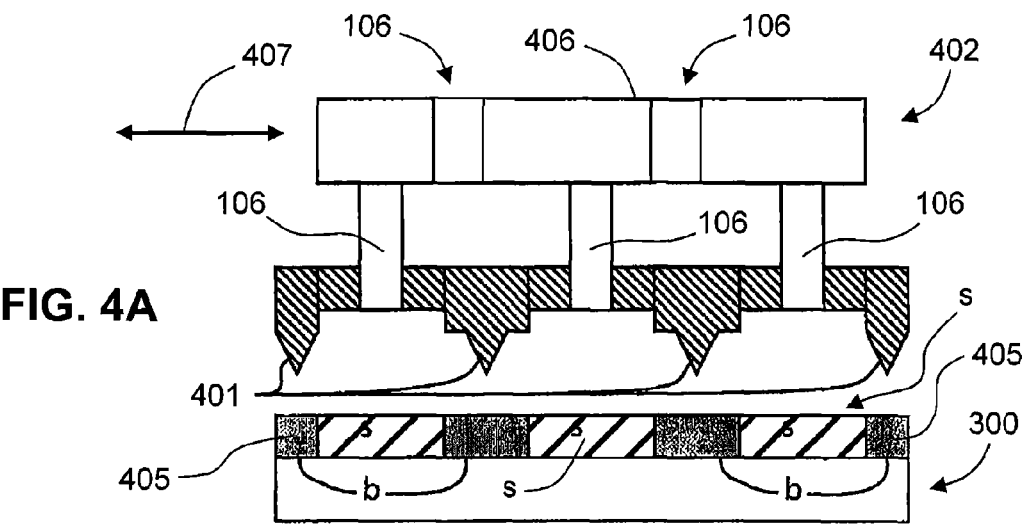
FIGS. 4A, B illustrate schematic side views of one embodiment of the isolation of each sample area of a sample library from adjacent sample areas.
Figure 4B:
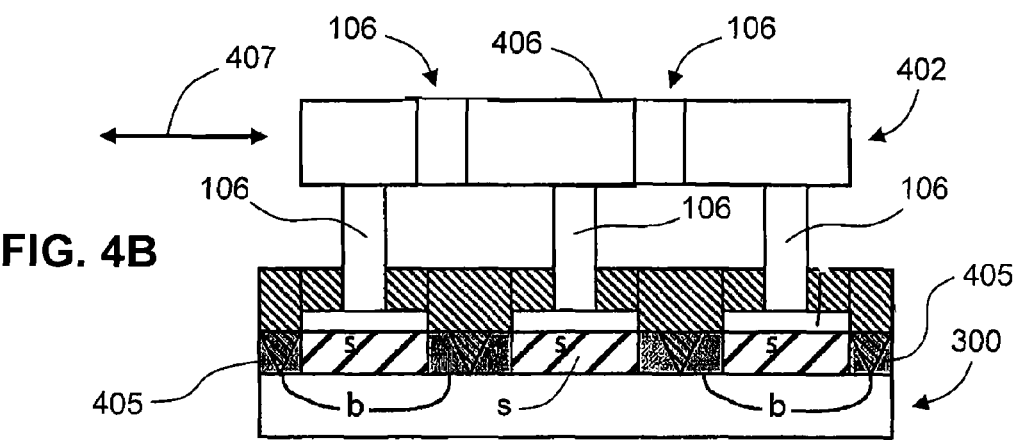

FIGS. 4A, B illustrate schematic side views of one embodiment of the isolation of each sample area s of sample library 300 from adjacent sample areas. In FIG. 4A, sample library 300 is positioned proximate to a sample receiver 402 in preparation for mounting thereon. In FIG. 4B, sample library 300 is shown mounted on sample receiver 402 and ready for sorption testing by gas sorption apparatus 100. In this embodiment, each sample area s is fluidly coupled to a dedicated low-volume conduit 106, and is fluidly isolated from adjacent sample areas s when sample library 300 is mounted on sample receiver 402. Sample receiver 402 is configured with an array of knife edges 401 that are aligned with isolation members 405, which are disposed on sample library 300. In this embodiment, isolation members 405 may be formed from a relatively soft material, such as copper, nickel, or a UHV-compatible polymer, and knife edges 401 may be a relatively hard material, such as stainless steel. Thus, when sample library 300 is mounted on sample receiver 402, knife edges 401 engage with isolation members 405 to fluidly isolate each of sample areas s. Alternatively, sample receiver 402 may not be configured with knife edges 401 and instead engages isolation members 405 with a substantially flat, polished surface to form the gas-tight seal. In another alternative embodiment, the surface of switchable manifold 101 may consist of an array of isolating rings, or squares of knife-edge raised material that press into isolation members 405, thereby isolating each sample area s from adjacent sample areas while fluidly coupling each sample area s to a corresponding low-volume conduit 106. In yet another embodiment, the entire substrate of the sample library 300 is composed of material softer than the knife-edge material 401, such that the knife-edge material is pressed into the substrate between the discretized sample areas s or through a non-discretized continuous sample s, thereby isolating each sample area s from adjacent sample areas while fluidly coupling each sample area s to a corresponding low-volume conduit 106. Sample receiver 402 also includes low-volume conduits 106 positioned between knife edges 401, and is fluidly coupled and decoupled from switchable manifold 101 by a sliding valve 406. Sliding valve 406 actuates to fluidly couple and decouple sample receiver 402 and any sample library mounted thereon by translating horizontally as indicated by arrow 407.

In one embodiment, array 102 in FIG. 1 includes sensors with an electrically responsive material to quantify the quantity of gas released from sample materials during sorption testing. As noted above, such sensors may include hydride-based sensors or more conventional gas detectors. In either case, exposure to and reaction with the dosing gas causes the electrically responsive material contained in the sensor to undergo a change in one or more electrical properties, such as resistivity or electrochemical potential. This change in electrical properties can then be used to quantify either the amount of dosing gas that has reacted with the electrically responsive material, or the concentration of dosing gas that is in fluid contact with the electrically responsive material. In either case, the quantity of gas released by a sample can be easily calculated.

Figure 5:
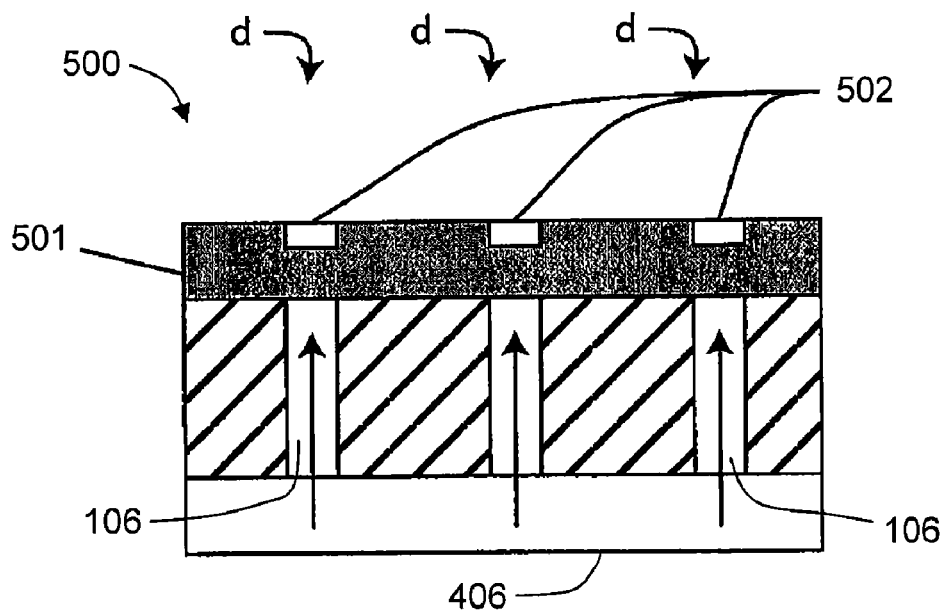
FIG. 5 is a schematic side view of a sensor array containing an electrically responsive material, according to an embodiment of the invention.

FIG. 5 is a schematic side view of a sensor array 500 containing an electrically responsive material 501, according to an embodiment of the invention. Sensor array 500 is one embodiment of array 102, and includes a plurality of sensors d, which are each fluidly coupled to a corresponding sample (not shown) via low-volume conduits 106 and a sliding valve 406. Each sensor d has a conductor 502 that provides a signal back to data collection system 114.

In one embodiment, array 102 in FIG. 1 includes sensors with an optically responsive material to quantify the quantity of gas released from samples material during sorption testing. As noted above, such sensors may include hydride-based sensors, where exposure to and reaction with hydrogen gas causes the optically responsive material contained in the sensor to undergo a change in one or more optical properties, such as reflectivity and/or transmissivity of visible light.

Figure 6:
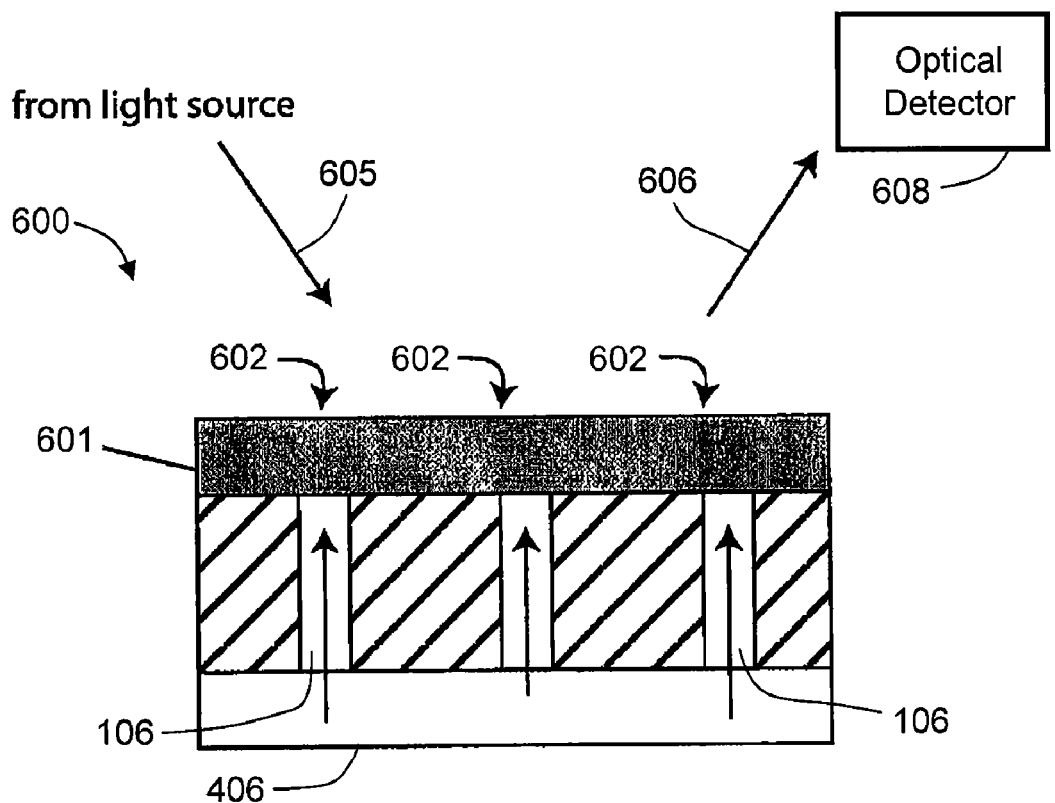
FIG. 6 is a schematic side view of a sensor array containing an optically responsive material, according to an embodiment of the invention.

FIG. 6 is a schematic side view of a sensor array 600 containing an optically responsive material 601, according to an embodiment of the invention. Sensor array 600 is one embodiment of array 102, and includes a plurality of sensors 602, which are each fluidly coupled to a corresponding sample (not shown) via low-volume conduits 106 and a sliding valve 406. In operation, illumination 605 from a light source is directed on sensors 602, and light 606 reflected from sensors 602 is collected by an optical detector 608. Optical detector 608 may be a digital camera that captures the condition of multiple sensors 602 with one or more images. The images are then stored in and/or processed by data collection system 114 in FIG. 1. Alternatively, optical detector 608 may include a plurality of light sensors, such as photocells, so that each sensor 602 has a corresponding and dedicated light sensor. Thus, the optical response from each sensor may be gathered either simultaneously or individually. As noted above, exposure to the dosing gas produces a change in the reflectivity and/or transmissivity of the optically responsive material, which is measured by optical detector 608 or detectors as described herein.

Figure 7:
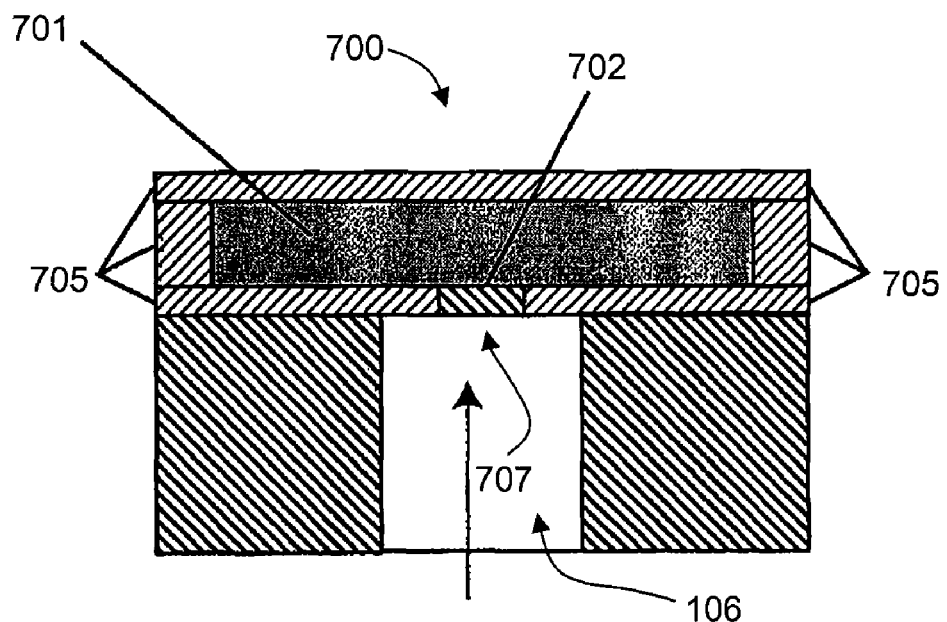
FIG. 7 is a schematic side view of another embodiment of a sensor that includes an optically responsive material and may be contained in a sensor array.

FIG. 7 is a schematic side view of a sensor that includes an optically responsive material 701 and may be included in array 102, according to an alternative embodiment of the invention. Similar to sensors 602, exposure of dosing gas to sensor 700 produces an optical response in optically responsive material 701 that can be detected and/or recorded by an optical detector. In sensor 700, however, optically responsive material 701 undergoes a distinct color, transparency and/or reflectivity change upon absorption of the dosing gas, rather than a gradual change in reflectivity or transmissivity as more dosing gas is absorbed. In this fashion, a clearly defined region of optically responsive material 701 changes color when sensor 700 is exposed to a dosing gas of the appropriate chemistry. For example, when the dosing gas being measured by sensor 700 is hydrogen, optically responsive material 701 may be a yttrium- or lanthanum-based compound. As is known in the art, such compounds can produce the distinct reflectivity change necessary for sensor 700 to function as contemplated herein.

To isolate optically responsive material 701 from ambient hydrogen and other contamination that may result in unwanted optical changes or passivation, sensor 700 includes a protective layer 705 that isolates optically responsive material 701. Layer 705 may be the native yttrium-oxide or a secondary deposited metal oxide or impermeable metal or polymer layer, which is known to prevent diffusion of hydrogen therethrough. Sensor 700 also includes a palladium orifice or window 702 deposited in and sealing opening 707 of protective layer 705, as shown. Thus, palladium orifice 702 prevents fluid contact between gases present in low-volume conduit 106 and optically responsive material 701 preventing oxidation or passivation of the responsive material 701 in sealing opening 707. However, since hydrogen readily diffuses through palladium, optically responsive material 701 should only be exposed to hydrogen that is introduced via low-volume conduit 106 and the palladium orifice 702. Sensor 700 responds to exposure to hydrogen by forming a circular reacted region of different color, transparency, or reflectivity centered over opening 707, where the diameter of the reacted region can be readily correlated to a quantity of hydrogen gas absorbed by sensor 700. The diameter of the reacted region in sensor 700 and the diameters of the reacted regions in all other sensors in the same sample library can then be recorded simultaneously by an optical detector, such as a digital camera. In this fashion, hydrogen released by a plurality of samples in sample library 300 can be simultaneously quantified, greatly speeding the screening process.

Figure 8:
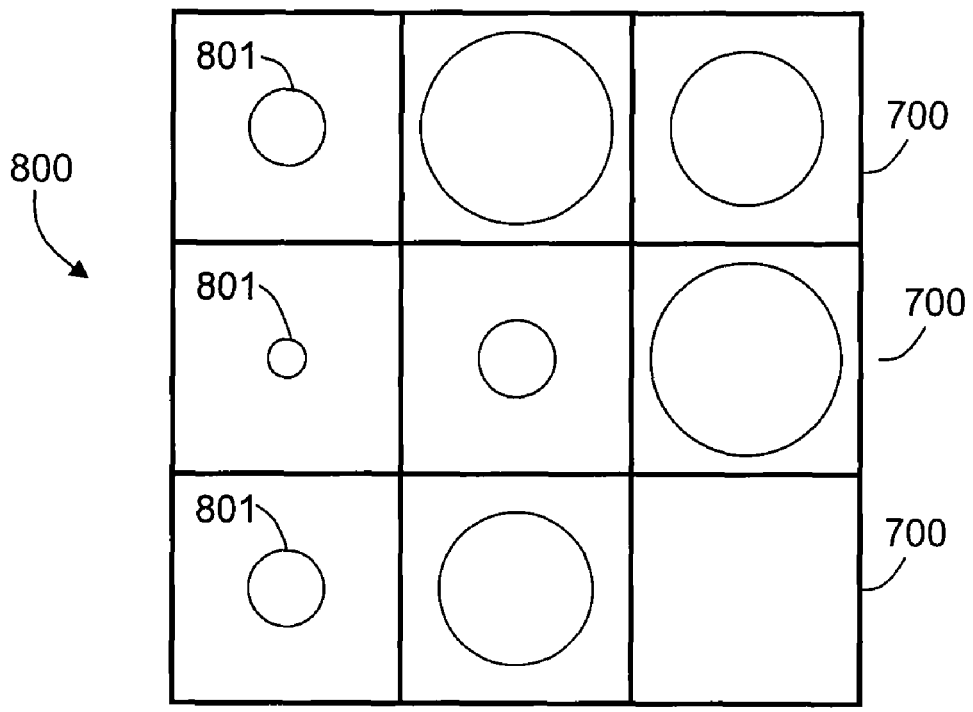
FIG. 8 illustrates a schematic top view of a sensor array containing a plurality of sensors after sorption testing.

FIG. 8 illustrates a schematic top view of a sensor array 800 containing a plurality of sensors 700 after sorption testing. As shown, circular regions 801 are visible and the diameters thereof are easily measured. Thus, desorbed gas concentrations of each sample may be correlated to gas over-pressure and temperature of each sample in a single or series of measurements.

In an alternative embodiment, the sensor array 800 may be pre-charged with gas to the fully absorbed state and then exposed to the sample array with each sensor acting as a gas source. The concentration of gas absorbed by each sample can be measured quantitatively by the diameter of the desorbed circular regions 801 of the sensor array 800. Additionally, measured increases (sample desorption) or decreases (sample absorption) of the diameter of the circular regions 801 with time may provide a measurement of the individual kinetics of gas desorption or sorption of the array of samples at a given temperature or with a controlled temperature ramping.

In one embodiment, a sensor array containing sensors d in FIG. 5, sensors 602 in FIG. 6, and/or sensor 700 in FIG. 7 may be formed on a silicon substrate or an optically transparent substrate such as glass. Deposition and etching processing techniques are well suited to efficiently fabricating a large number of very small sensors on a single substrate, thereby facilitating the screening of large numbers of different material compositions. Sensors containing either electrically and/or optically responsive material, can be formed in this manner.

In one embodiment, a sensor array, such as sensor array 102, may be mounted to switchable manifold 101 in FIG. 1 using the same techniques described above for sample library 300, so that each sensor is fluidly isolated from each adjacent sensor, but is fluidly coupled to a corresponding sample material.

In one embodiment, hydride-based sensors may be used as mini-reservoirs of hydrogen gas and can therefore be used as "mini-dosers." For example, sensor array 800 can be dosed with hydrogen such that each sensor 700 contains a known quantity of hydrogen gas. Sample materials in a sample library can then be fluidly coupled to vacuum source 105 of FIG. 1 and/or heated, as necessary, to release the hydrogen or contaminants contained in each sample material. Sensors 700 are fluidly coupled to the sample library and heated, as required, to release hydrogen therefrom. Sorption of hydrogen into each sample can then be readily quantified by comparing the quantity of hydrogen actually released by each sensor 700. Because the hydrogen content of each sensor 700 is measured optically, which, again, can be done quickly and accurately, measurements of the hydrogen content of the sensors 700 can be performed multiple times throughout the life of a given test. This approach allows the simultaneous collection of kinetic and thermodynamic stability information for a large number of material samples simultaneously. In one embodiment, one or more of the samples so tested may be a control sample, comprising a material that is known to absorb no hydrogen. Such control samples may be used to assist in the calibration of sorption tests by quantifying how much hydrogen is present in a low-volume conduit 106 at a specific pressure and temperature and at any time during the sorption test.

While the foregoing is directed to embodiments of the present invention, other and further embodiments of the invention may be devised without departing from the basic scope thereof, and the scope thereof is determined by the claims that follow.

I claim:

1. An apparatus for performing multiple gas sorption measurements simultaneously, comprising:
   a switchable manifold;
   an array of sensors fluidly coupled to the switchable manifold and including a first sensor and a second sensor;
   an array of samples fluidly coupled to the switchable manifold and including a first sample and a second sample;
   a first low-volume conduit configured to fluidly couple the first sensor to the first sample; and
   a second low-volume conduit configured to fluidly couple the second sensor to the second sample.

2. The apparatus of claim 1, wherein the first and second low-volume conduits have an inner diameter no greater than about 2 mm.

3. The apparatus of claim 2, wherein a portion of each of the first and second low-volume conduits comprises tubing.

4. The apparatus of claim 2, wherein a portion of each of the first and second low-volume conduits comprises holes formed in a body portion of the switchable manifold.

5. The apparatus of claim 4, wherein a portion of the switchable manifold comprises a thermally insulative material.

6. The apparatus of claim 5, wherein the thermally insulative material is selected from the group consisting of alumina and glass.

7. The apparatus of claim 1, wherein the switchable manifold is configured to fluidly couple the first sensor to the first sample and the second sensor to the second sample simultaneously.

8. The apparatus of claim 1, further comprising a first heater in thermal contact with the first sample.

9. The apparatus of claim 8, further comprising a second heater in thermal contact with the first sensor.

10. The apparatus of claim 9, further comprising a third heater in thermal contact with the second sensor.

11. The apparatus of claim 1, wherein the switchable manifold is configured to fluidly couple the first and second sensors to a dosing gas source and to a vacuum source.

12. The apparatus of claim 1, wherein the switchable manifold is configured to fluidly couple the first and second samples to a dosing gas source or to a vacuum source.

13. The apparatus of claim 1, wherein the first sensor comprises a material that is electrically responsive in the presence of a dosing gas.

14. The apparatus of claim 1, wherein the first sensor comprises a material that is optically responsive in the presence of a dosing gas.

15. The apparatus of claim 14, wherein the material comprises a hydride-forming material.

16. The apparatus of claim 1, wherein the first sensor and the second sensor are disposed on a single substrate.

17. The apparatus of claim 16, wherein the first sensor and the second sensor are formed together on the substrate.

18. The apparatus of claim 1, wherein first and second the low-volume conduits having a free volume no greater than about 0.1 ml.

19. The apparatus of claim 1, wherein the first sample and the second sample are disposed within a sample library.

20. The apparatus of claim 19, wherein the sample library comprises a single substrate.

21. The apparatus of claim 19, wherein the sample library comprises an isolation member, and the isolation member forms a gas-tight seal between the switchable manifold and the sample library.

22. The apparatus of claim 19, wherein the first sample comprises a material having known sorption properties.

* * * * *